United States Patent [19]

Shurtleff

[11] 4,041,762

[45] Aug. 16, 1977

[54] SWING CHUTE SAMPLER

[75] Inventor: George S. Shurtleff, Coon Rapids, Minn.

[73] Assignee: Baker Oil Tools, Inc., Los Angeles, Calif.

[21] Appl. No.: 622,660

[22] Filed: Oct. 15, 1975

[51] Int. Cl.² ............................................. G01N 1/04
[52] U.S. Cl. .................................... 73/422 R; 137/612
[58] Field of Search ............. 73/422 R, 421 R, 421 B, 73/424; 137/611, 610, 612

[56] References Cited

U.S. PATENT DOCUMENTS

| | | | |
|---|---|---|---|
| 416,402 | 12/1889 | Davis | 137/611 |
| 427,206 | 5/1890 | Suddick | 137/611 |
| 876,687 | 1/1908 | Brown | 137/612 |
| 3,006,367 | 10/1961 | Thompson | 73/422 R |

Primary Examiner—S. Clement Swisher
Assistant Examiner—Denis E. Corr
Attorney, Agent, or Firm—Trask & Britt

[57] ABSTRACT

A swing chute sampler for diverting the flow of material from a mainstream comprising an external housing having upper and lower openings, a side-arm chute, a fixed internal chute and an internal swing chute pivoted near the upper edge of the opening in the main housing which communicates with the side-arm chute is described. The fixed internal chute is substantially axially aligned with the main housing and has an upper and lower opening, said lower opening preferably being below the upper edge of the side opening in the main housing. The swing chute is of the same general cross-sectional shape as the fixed internal chute and is pivoted about one of its upper edges at the junction of the upper edge of the side opening in the housing so that the swing chute can pivot from a pass-through position substantially axially aligned with the main housing wherein the upper opening of the swing chute overlaps the lower portion of the internal chute so that material falling through the internal chute passes through the swing chute and discharges from the lower opening of the main housing. The swing chute is rotatable about a lateral pivot point to a sampling position wherein the swing chute is substantially axially aligned with the side-arm chute and wherein the upper opening of the swing chute only slightly overlaps the lower portion of the internal chute and the lower opening of the swing chute is disposed within the side-arm chute so that material falling through the internal chute passes through the swing chute and discharges from the lower opening of the side arm chute without any material discharging from the lower opening of the main housing.

10 Claims, 4 Drawing Figures

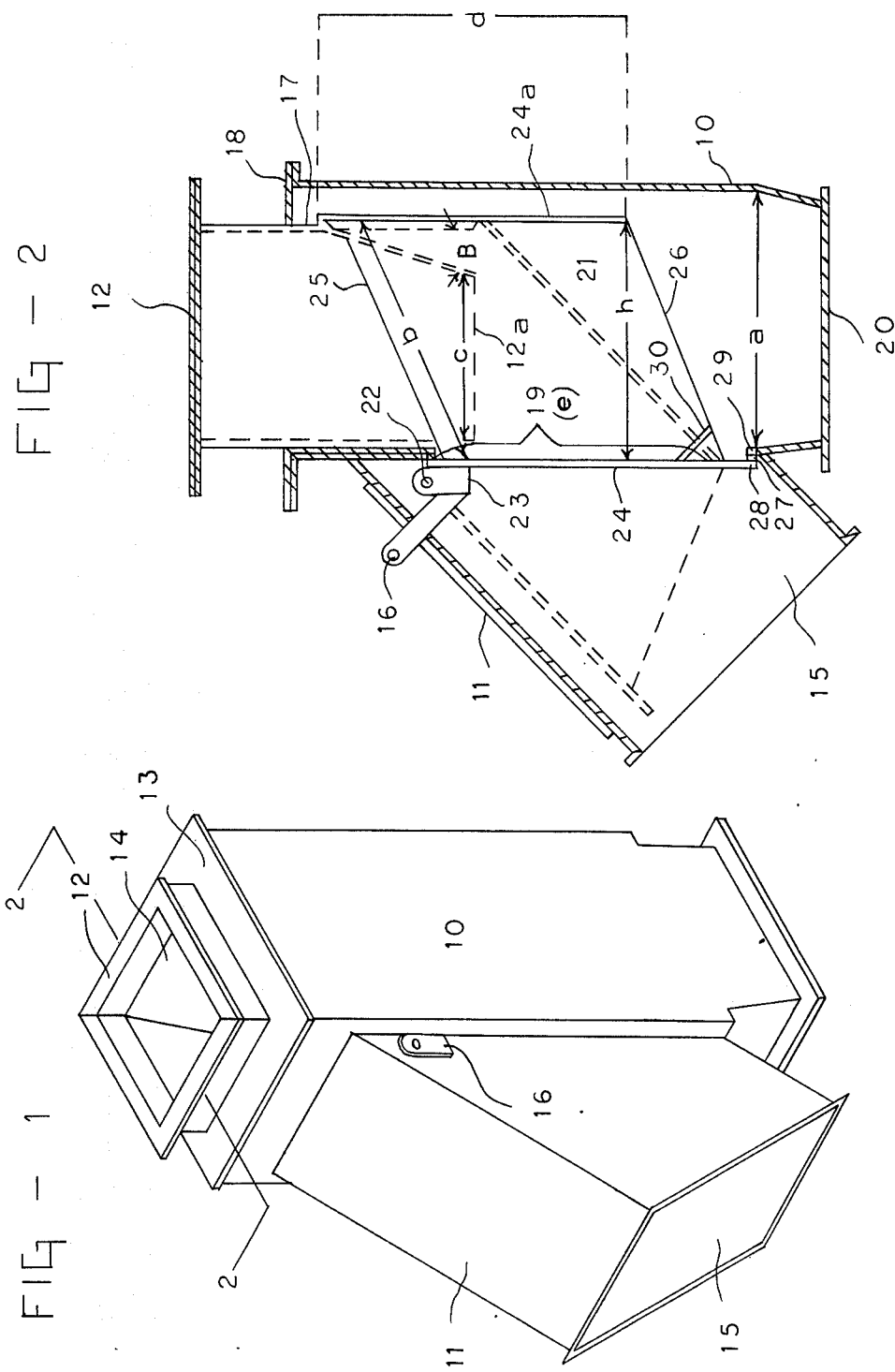

SWING CHUTE SAMPLER

BACKGROUND OF THE INVENTION

1. Field

The invention relates to sampling apparatus for removing a portion of the particulate matter from a stream of particulate material for sampling moisture and other physical characteristics and chemical composition. Samplers of this type are particularly useful in sampling streams of finely divided coal so that the moisture content, BTU content, sulfur content and the like may be determined. The sample removed from the mainstream must be representative of the material in the mainstream, that is, it is desirable that fine material not be lost during the collection of the sample.

2. Prior Art

A number of different devices have been utilized to divert particulate matter from a mainstream into a secondary stream so that the sample of the material in the mainstream may be taken. One widely utilized device for this purpose is the flop-gate.

A typical flop-gate construction comprises a main duct disposed vertically and having a square or rectangular cross-section. In one of the vertical walls a door is fitted which is pivoted along its lower edge. The width of the door is substantially the same as the width of the duct and the height of the door is greater than the width of the duct. Whenever it is desired to take a sample, the door is swung inward by pivoting about its lower edge so that it swings into the duct and substantially closes the duct to the flow of material as the material strikes the face of the door and discharges through the side opening in the duct into a sampling chute. The flop-gate is simple in construction. However, the device has disadvantages inasmuch as the door or gate cannot fit so tightly against the interior walls of the main duct to prevent a substantial amount of fine material from passing around the door. Also, since the gate closes against the stream of material it frequently does not close tight because it catches material between the upper edge of the door and the interior of the duct so that some material leaks into the sampler chute at times other than the sampling period.

OBJECTIVES OF THE INVENTION

It is an object of the instant invention to provide a swing chute sampler which is of simple construction and function.

It is a further object of the invention to provide a sampler which efficiently diverts all of the particulate matter from a mainstream to a sampler stream and which does not permit the diversion of material into the sample chute during periods when the swing cute is in a non-sampling position.

A further object of the invention is to provide a swing chute sampler wherein the position of the swing chute may be detected from the external appearance of a sampler lever and wherein the sampler forms a substantially dust-free enclosure thereby precluding the escape of sample material or the introduction of moisture laden air into the sampler.

SUMMARY OF THE INVENTION

A swing chute for diverting the flow of particulate material from a mainstream into a side sampler stream is described. The sampler comprises an external housing and a side-arm chute communicating with an opening in the side of said housing. In the housing is disposed a fixed internal or insert chute which is substantially axially aligned with said housing and which has an upper and lower opening. The insert chute is sealed within the upper opening of the housing so that the only opening by which material may flow into the housing is through the upper opening of the insert chute. The lower opening of the insert chute is preferably below the upper edge of the side opening within the housing. The lower opening of the insert chute is smaller than the cross-section of the housing.

An internal swing chute is fitted within the housing so that it can occupy two extreme positions. The swing chute has an upper and lower opening and a general cross-sectional shape which is the same as the fixed internal chute. The upper opening of the swing chute is slightly larger than the lower opening of the insert chute and in a pass-through position the swing chute, which is pivoted at an upper edge, is in a position so that the upper opening of a swing chute encompasses a substantial portion of the lower part of the insert chute and the lower opening of the swing chute is aligned with the lower opening of the housing. The swing chute in the pass-through position, which is a position in substantial axial alignment with the housing also seals off the wall opening in the housing. In the other position, or sampling position, the swing chute is substantially axially aligned with the side-arm chute so that the upper opening of the swing chute overlaps only slightly the lower portion of the insert chute and the lower opening of the swing chute is within the side-arm chute. In the sampling position, material falling down the fixed internal chute passes through the swing chute, out the lower opening of the swing chute and is discharged through the lower opening of the side-arm chute.

DESCRIPTION OF FIGURES

The instant invention is illustrated by the following drawings wherein,

FIG. 1 is a perspective overal view of the swing chute sampler;

FIG. 2 is a sectional elevational view along section lines 2—2 of FIG. 1;

DESCRIPTION OF THE INVENTION

Figure 4:
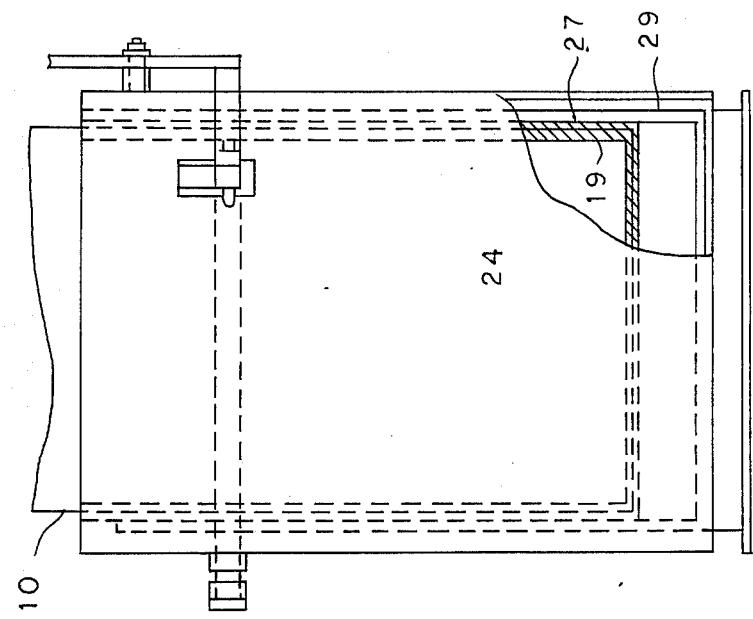
FIG. 4 is an elevational view of the side chute of the swing chute sampler.

In FIG. 1 an overall view of the swing chute sampler is provided in which the main housing 10 is illustrated with the side-arm chute 11 attached thereto at an angle preferably not greater than about 45° to the horizontal. The fixed insert or internal chute 12 is illustrated protruding from the flanged top 13 of housing 10. The upper inlet opening 14 of the fixed insert chute 12 is shown along with the discharge opening 15 of the side-arm chute. Lever 16 is attached to the axle fastened to the swing chute and is used to position the swing chute in either a pass-through position or a sampling position and to indicate position of the internal swing chute.

The functioning of a swing chute sampler can be seen clearly in FIG. 2 wherein the housing 10 having an upper opening 17 which is covered with a flange 18 through which the fixed insert chute 12 passes. A side opening 19 is present in one side wall of the main housing 10. The discharge opening of the housing 20 is in vertical alignment with the upper opening 18 of the housing and the upper opening 14 and lower opening 12a of the fixed insert chute. The internal swing chute 21 is pivoted about lateral axle 22. A hinge 23 is attached to forward side wall 24 of the internal chute and the axle 22 is attached through a side wall of the side chute at the upper edge of opening 19. The rims of upper opening 25 and lower opening 26 of the swing chute are preferably parallel and are disposed at an acute angle. The side-arm chute 11 attaches at an angle to the side wall of the housing 10 completely encompasses the opening 19. The fixed internal chute 12 projects down into the housing well below the upper edge of opening 19. The lower opening 12a of the fixed internal chute is of a substantially smaller cross-section than the internal cross-sectional area of the housing 10.

The relationship of some of the dimensions of the parts of the swing chute sampler is important in that certain clearances must be maintained to maintain the proper sealing effect. The width of the internal housing is represented by the letter $a$ while the width of the fixed internal chute at the lower opening is designated $c$ and the width of the upper opeining of the swing chute along the diagonal is illustrated as $b$. The opening of the internal chute $c$ is less than the opening of the swing chute $b$ which is less than the opening or the width of the internal housing $a$. The width of the swing chute is illustrated as $h$ which is less than the length of opening 19 illustrated as $e$. The width $h$ is less than the width $e$ which is less than the length $d$ of the swing chute.

The embodiment illustrated in FIG. 2 possess a forward wall 24 of the internal swing chute 21 is preferably slightly longer than the rear wall 24a and is slightly longer and wider than opening 19 so that the opening 19 may be sealed when the swing chute is in a vertical or non-sampling position. To improve the seal between sidewall 24 and the rim encircling opening 19 a sealing strip 27 which encompasses opening 19. A rim portion 28 of sidewall 24 extends in overlapping relationship to a lip 27 of the sidewall of housing 10 which supports sealing strip 27.

A fillet strip 30, or deflection plate, is angulary positioned on the interior of swing chute 21 near the base of sidewall 24 so that opening 26 is slightly reduced and particulate material falling down chute 21 is diverted into housing 10 as chute 21 approaches its vertical position to facilitate sealing between rim 28 and lip 29 without particulate matter falling into the gap therebetween. Sidewalls 24b and 24c of swing chute 21 join forward and rear walls 24 and 24a to form the body of cute 21. The sidewalls 24b and 24c are angularly cut at the bottom and top at an acute angle, which will depend upon the width and height of the chute, but generally between 15° and 30°. The angular aspect of sidewalls 24b and 24c is necessary so that the bottom of rearwall 24a will clear lip 27 when the swing chute 21 is in a sampling position.

The fixed insert chute 12 preferably has a rearwall 12b which is slanted to provide a bottom opening which is smaller than its upper opening. As seen in FIG. 2, the slanting rear wall of the fixed insert chute 12 directs particles in contact therewith down the rear wall 24a of swing chute 21 when swing chute 21 is in a sampling position.

Figure 3:
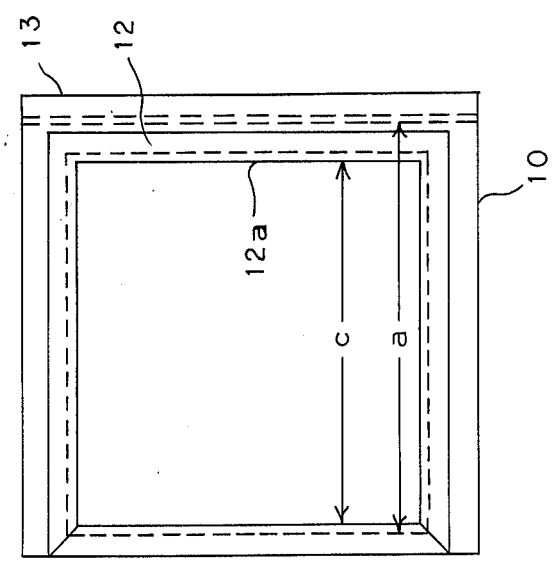
FIG. 3 is a plan view of the swing chute sampler.

The relationship of the openings of housing 10 and the fixed insert chute 12 is illustrated in FIG. 3. The lower opening of fixed chute 12 has a width $c$ which is substantially less than the width of the housing opening $a$.

The relationship of the vertical opening is illustrated in FIG. 4 which shows the side chute 11 as being substantially larger than forward wall 24 of the swing chute. Opening 19 is smaller than forward wall 24 and has a sealing strip 27 which encompasses it. A lip 29 extends around the interior of side chute 11.

I claim:
1. A swing chute sampler for particulate material comprising:
   a. an external housing having upper and lower openings and a side-arm chute communicating with an opening in the side of said housing,
   b. a fixed internal chute disposed at least partially within the upper portion of said housing and having an upper opening and a lower opening, the upper opening of said internal chute sized to communicate with a feed chute and sealed within the upper opening of the housing, said fixed chute extending below the upper edge of the side arm opening of the housing,
   c. a swing chute having an upper opening and a lower opening and a cross-section of the same general shape as said internal chute, said swing chute having hinge means to pivot said chute at the upper edge of its forward wall near the junction of the upper edge of the side opening in the housing, said swing chute dimensioned to pivot about its attachment to the housing to move from a first position wherein the upper opening of said swing chute communicates with and slightly overlaps the lower opening of said internal chute and said lower opening communicates with said side opening so that material falling down said internal chute is diverted to said side arm chute and a second position wherein said swing chute is substantially axially aligned with said fixed internal chute, its upper opening encompassing the lower portion of said internal chute and substantially overlapping same and its lower opening removed from said-arm chute so that material falling down said internal chute passes through said swing chute and through the lower opening of said housing, said swing chute having sealing means to seal the lower edge of said side opening when said swing chute is in said second position.

2. The swing chute sampler of claim 1 wherein the cross-section of said housing, said swing chute and said side-arm opening is quadrangular.

3. The swing chute sampler of claim 1 wherein the forward wall of said swing chute forms a sealing relationship with said side arm opening when said swing chute sampler is axially aligned with said fixed internal chute.

4. The swing chute sampler of claim 1 wherein the lower opening of said fixed chute is smaller than its upper opening and at least the rear wall of said fixed chute slopes inwardly towards said lower opening.

5. The swing chute of claim 1 wherein the rear wall of said swing chute is displaced vertically above said forward wall and the openings in said swing chute slope upwardly from the forward wall to said rear wall.

6. The swing chute sampler of claim 1 wherein said swing chute swings through an arc of not greater than about 45° in moving from its first position to its second position.

7. The swing chute sampler of claim 1 wherein the distance between the forward and rear walls of the swing chute must be substantially greater than the distance between the forward and rear walls of the fixed chute near the bottom opening of the fixed chute.

8. The swing chute of claim 3 wherein said forward wall of said swing chute has a length greater than the height of said side arm opening.

9. The swing chute of claim 1 wherein said hinge means of the swing cute is displaced forward slightly of the forward wall of said swing chute.

10. The swing chute of claim 1 wherein said swing chute has a deflection plate located between the sidewalls and along the interior of the forward wall of the swing chute near the lower edge of said swing chute to divert particles falling through said swing chute towards the lower opening of said housing when said swing chute is substantially axially aligned with the upper and lower openings of said housing.

* * * * *

UNITED STATES PATENT OFFICE
CERTIFICATE OF CORRECTION

Patent No. 4,041,762　　　　　　　　　Dated August 16, 1977

Inventor(s) George S. Shurtleff

It is certified that error appears in the above-identified patent and that said Letters Patent are hereby corrected as shown below:

Column 1, line 54, change "cute" to ---chute---;

Column 2, line 40, change "overal" to ---overall---;

Column 3, line 9, after the numeral 10, add the word ---and---;

Column 3, line 67, change "opening" to ---openings---.

Signed and Sealed this

Seventh Day of March 1978

[SEAL]

Attest:

RUTH C. MASON
*Attesting Officer*

LUTRELLE F. PARKER
*Acting Commissioner of Patents and Trademarks*